United States Patent [19]

Bellin et al.

[11] Patent Number: 5,193,549
[45] Date of Patent: Mar. 16, 1993

[54] INFLATABLE CUFF

[75] Inventors: Matthew Bellin, Burnsville; Susan Brunsvold, Minneapolis; John Moberg, Plymouth, all of Minn.

[73] Assignee: Biomedical Dynamics Corporation, Minneapolis, Minn.

[21] Appl. No.: 551,527

[22] Filed: Jul. 11, 1990

[51] Int. Cl.[5] .................. A61B 5/022; A61B 17/12; A61F 5/30
[52] U.S. Cl. .................. 128/686; 128/677; 128/DIG. 20; 606/202; 156/304.6
[58] Field of Search .................. 128/87 R, 89 R, 90, 128/155, 156, 165, 677, 686, 846, 847, 878, 882, 887, DIG. 20; 604/391; 383/3; 156/308.4, 304.1, 304.6; 606/202, 203

[56] References Cited

U.S. PATENT DOCUMENTS

| | | | |
|---|---|---|---|
| 1,827,241 | 10/1931 | Kempf | 606/202 |
| 1,970,042 | 8/1934 | Brathwaite | 128/327 |
| 2,029,912 | 2/1936 | Cossor | 128/327 |
| 2,618,269 | 11/1952 | Baum et al. | 128/327 |
| 2,714,379 | 8/1955 | Raines | 128/2.05 |
| 2,758,593 | 8/1956 | Berman | 128/2.05 |
| 3,095,873 | 7/1963 | Edmunds, Jr. . | |
| 3,279,459 | 10/1966 | Schenker | 128/165 |
| 3,454,010 | 7/1969 | Lilligren et al. | 606/202 |
| 3,467,077 | 9/1969 | Cohen | 128/2.05 |
| 3,473,525 | 10/1969 | Hanafin | 128/2.05 |
| 3,504,675 | 4/1970 | Bishop, Jr. | 128/327 |
| 3,570,495 | 3/1971 | Wright | 128/327 |
| 3,603,304 | 9/1971 | Werner et al. . | |
| 3,606,880 | 9/1971 | Ogle, Jr. | 128/2.05 |
| 3,633,567 | 1/1972 | Sarnoff | 606/202 |
| 3,654,931 | 4/1972 | Hazelwood | 128/327 |
| 3,669,096 | 6/1972 | Hurwitz | 606/202 |
| 3,670,735 | 6/1972 | Hazelwood | 128/327 |
| 3,717,145 | 2/1973 | Berndt et al. | 128/DIG. 20 |
| 3,756,239 | 9/1973 | Smythe . | |
| 3,757,772 | 9/1973 | Goldblat et al. | 128/2.05 |
| 3,760,795 | 9/1973 | Adelhed | 128/2.05 |
| 3,765,405 | 10/1973 | Natkanski | 128/2.05 |
| 3,771,515 | 11/1973 | Hurwitz . | |
| 3,773,036 | 11/1973 | Weyer | 128/2.05 |
| 3,977,393 | 8/1976 | Kovacic | 128/2.05 |
| 4,106,499 | 8/1978 | Ueda | 606/202 |
| 4,211,825 | 7/1980 | Shipman . | |
| 4,285,744 | 8/1981 | Rudolf et al. . | |
| 4,313,777 | 2/1982 | Buckley et al. . | |
| 4,354,503 | 10/1982 | Golden | 128/686 |
| 4,410,575 | 10/1983 | Obayashi et al. . | |
| 4,465,076 | 8/1984 | Sturgeon | 128/686 |
| 4,548,249 | 10/1985 | Slaughterbeck . | |
| 4,572,205 | 2/1986 | Sjonell | 128/686 |
| 4,605,010 | 8/1986 | McEwen | 128/686 |
| 4,628,918 | 12/1986 | Johnson, Jr. | 128/89 R |
| 4,637,394 | 1/1987 | Racz et al. | 606/202 |
| 4,716,906 | 1/1988 | Ruff | 128/686 |
| 4,727,885 | 3/1988 | Ruff | 128/686 |
| 4,838,276 | 6/1989 | Nagai et al. | 128/686 |
| 4,920,971 | 5/1990 | Blessinger | 128/686 |
| 4,971,044 | 11/1990 | Dye | 128/89 R |
| 4,979,953 | 12/1990 | Spence | 606/202 |
| 5,025,781 | 6/1991 | Ferrari | 128/DIG. 20 |

FOREIGN PATENT DOCUMENTS 8300426  2/1983  European Pat. Off. ............ 606/202

*Primary Examiner*—Lee S. Cohen
*Assistant Examiner*—Krista M. Pfaffle
*Attorney, Agent, or Firm*—Kinney & Lange

[57] ABSTRACT

Disclosed is a bladderless inflatable cuff comprising an inner compartment defined by a film, said inner compartment being closed except for an opening through which air may enter and exit said compartment, and an outer compartment comprising a loop portion of hook and loop fabric, said outer compartment serving as a container to limit the amount of expansion of said inner compartment when said inner compartment is inflated, and a fastener mounted on said outer compartment for fastening said cuff around a human body portion when in use.

14 Claims, 1 Drawing Sheet

INFLATABLE CUFF

FIELD OF THE INVENTION

The present invention relates to an inflatable cuff that may be secured around a human body part such as the upper arm when taking a blood pressure reading or around a leg having a fracture. The present invention more particularly relates to a bladderless cuff.

BACKGROUND OF THE INVENTION

Inflatable cuffs have been known for many years and have been used for a variety of purposes. For example, blood pressure readings have for many years been measured using an inflatable cuff to apply pressure to blood vessels and determining at what pressure blood will flow through the arteries. In so doing the health practitioner listens to the flow of blood while gradually decreasing the pressure applied by the cuff. A pressure gauge associated with the inflatable cuff indicates the applied pressure.

Inflatable cuffs have been used for other purposes, for example, such cuffs are used as splints to restrict the use of the limb of a patient with a fractured arm or leg.

Prior inflatable cuffs have generally been of two types, bladder-type cuffs and bladderless-type cuffs. In the first type, a cuff is made of fabric such as nylon and a bladder is removably inserted in the fabric cuff. The second type generally has a film or film/fabric laminate which is welded to produce an air holding cuff. The existing inflatable cuffs generally use small patches of hook and loop fabric to fasten the cuffs around the patient's arm.

The existing inflatable cuffs have had certain inherent disadvantages and problems. Prior cuffs which have been made of a film material have a feel which is sticky and unpleasant. There is little room for breathing between the cuff and the patient's skin therefore perspiration accumulates between the skin and the cuff. The perspiration creates a feeling of discomfort. If the cuff is to remain in place for an extended period of time, microbial materials may grow in the perspiration, producing irritation and/ or odor. The strength of the film has its own limitations. If over inflated the cuff may burst. The film/nylon fabric cuff likewise has little breathing capability. The bladder-type cuff has a fabric jacket that permits breathing but tends to be bulky and often is not very comfortable. The bladdertype structure results in a high cost product.

The present invention over comes the problems inherent in the prior inflatable cuffs.

SUMMARY OF THE PRESENT INVENTION

The present inflatable cuff is soft and absorbent, thus is more comfortable to the patient. The present invention may be used as a blood pressure cuff, a limb splint, surgical tourniquet, or anti-shock trousers.

The present invention provides an inflatable cuff having an inner compartment defined by a film. The inner compartment is closed- except for an opening through which air may enter and exit the compartment. The present invention has an outer compartment formed of an open weave fabric which may be a loop fabric. The loop fabric may be any loop portion of the combination product known as "hook and loop fabric" such as the commercially available Velcro ®. The open weave fabric e.g. loop fabric, tends to be thick and soft thus providing comfort when compared to prior cuffs.

The outer compartment serves as a container to limit the amount of expansion of said inner compartment when the inner compartment is inflated and serves as a soft breathing layer between the cuff and the body surface of the patient on which the cuff is used. A fastener is mounted on the outer compartment for fastening the cuff around a human body portion when in use. The fastener may be the hook fabric which is associated with the loop fabric. The hook fabric is engageable with the loop fabric to secure the cuff in a tubular configuration.

The present invention may be formed from a pair of inner sheets of film and a pair of outer sheets of loop fabric. Alternatively, the present cuff may be formed of two sheets, e.g., a film sheet and a fabric sheet. The two sheets are folded to make a sandwich with the film forming two inner layers and the fabric forming a pair of outer layers. The inner compartment may have three edges which are sealed by welding the film to itself with high energy electromagnetic waves. The inner compartment and the outer compartment may be secured together, for example, along the three exposed edges formed by superimposing a sheet of the loop fabric over a sheet of the film and overlaying a first half of said superimposed sheets over a second half of said superimposed sheets and applying high energy electromagnetic waves to weld overlaying superimposed sheets along the three edges.

The electromagnetic welding embeds the fabric in the film at the weld line. The electromagnetic welding eliminates the need to use adhesives to secure the fabric to the film, reducing the cost and providing a better product.

IN THE DRAWINGS

DETAILED DESCRIPTION OF THE INVENTION

Figure 1:
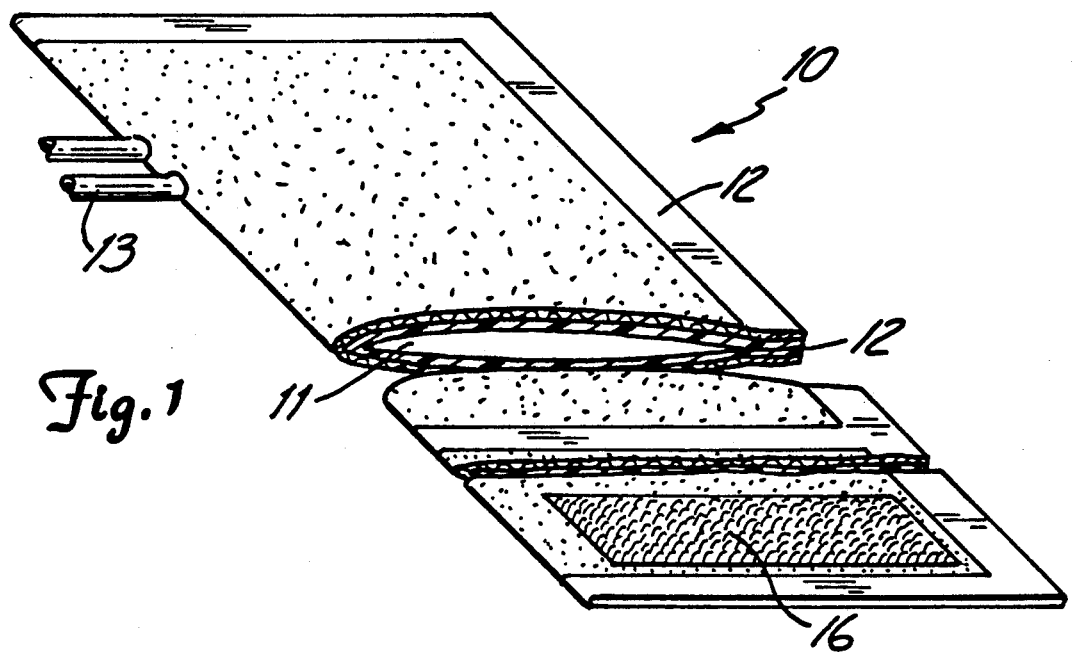
FIG. 1 shows a perspective view of the present inflatable cuff with portions broken away to show under lying structure.
Figure 2:
FIG. 2 shows an exploded view of the superimposed sheets forming the present cuff with the folded sheets shown in broken lines.
Figure 3:
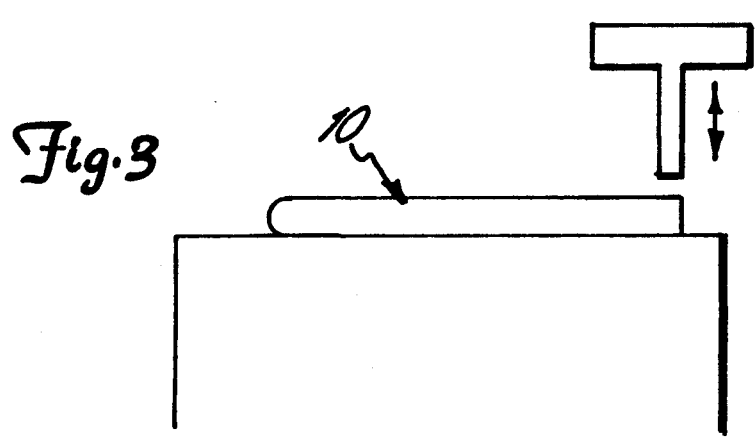
FIG. 3 illustrates apparatus applying electromagnetic waves to the superimposed sheets during welding of the sheets to form the cuff.

The inflatable cuff 10 of the present invention, a preferred embodiment is shown in FIG. 1 includes an inner compartment 11 that is formed of sheet film material. The sheet film material may be of any suitable polymer such as polyvinylchloride or polyurethane, or the like. The sheet film material may be sealed around the periphery such as by the welding 12. The cuff compartment 11 is closed except for a tube 13 through which air may enter and exit the compartment 11.

The cuff 10 has an outer compartment 14 which encloses the inner compartment 11. The outer compartment 14 is formed of an open weave fabric preferably loop fabric. The term "loop fabric" as used herein refers to the loop portion of the combination commonly referred to as "hook and loop fabric." Any of various commercially available loop fabric may be used such a Velcro ® loop fabric. The outer compartment 14 serves as a soft fabric surface for contact with human body portion. The outer compartment 14 further serves as a container to limit the amount of expansion of said inner compartment 11 when said inner compartment 11 is inflated. The loop fabric may also be secured around the edges by welding.

A fastener 16 is mounted on the outer compartment 14 for fastening the cuff 10 around the human body portion when in use. The fastener 16 may be hook fabric, the hook fabric being interengageable with said loop fabric.

The cuff 10 may be formed by over laying a sheet of film over a sheet of loop fabric. The two sheets may be of approximately the same size. The two sheets may be simultaneously cut to approximately the same size. If desired the film and fabric may be tacked together for example by welding a plurality of spots prior to the cutting process, thereby forming a composite sheet. The composite of the two sheets may be manipulated with a first half of said composite sheet over lying the second half of the composite. The sheets may then be welded along the open edges with high energy electromagnetic waves. The inner compartment and the outer compartment may be secured together along the three exposed edges by the welding processes. The hook fabric may also be secured to the loop fabric by welding.

The method of the present invention includes preparing an inflatable cuff by first cutting a sheet of film and a sheet of loop fabric to a desired size. The two sheets, either before or after welding are overlaid with the film sheet placed on the loop fabric sheet. The resulting composite sheet, after being cut to size, is adjusted so that a first half of the composite sheet lies over the second half of the composite sheet. A high energy electromagnetic wave is applied to the raw edges of said overlaying composite sheet thereby welding the raw edges and fusing the edge portions of the loop fabric and film together forming an inner compartment defined by the film and an outer compartment comprising the loop fabric portion of hook and loop fabric. The inner compartment being closed except for an opening through which air may enter and exit the compartment. The outer compartment serves as the container to limit the amount of expansion of said inner compartment when said inner compartment is inflated. Next the fastener is secured on the outer compartment such as by welding, adhesive or sewing. A similar process is followed when forming the cuff from four sheets except the step of folding is not included.

The method includes welding of the composite sheet using electromagnetic wave energy at any suitable frequency such as a frequency of about 23 megahertz which is an FCC approved frequency. The method may use electromagnetic wave energy at any suitable power that will provide the necessary energy to securely bond the sheets. The power may be at a wattage of one to eight kilowatts. The method includes applying the high energy electromagnetic wave to the raw edges of said overlaying composite sheet thereby welding said raw edges and fusing the edge portions of the loop fabric and film together forming an inner sealed compartment defined by said film.

While certain preferred embodiments of the present invention have been disclosed herein it is to be recognized that various modifications may be made without departing from the broader scope of the present invention.

What is claimed is:

1. An inflatable cuff comprising:
   an inner compartment being defined by an air-impermeable film and being closed except for an opening through which air may be caused to enter and exit the compartment;
   an outer compartment being entirely defined by a loop fabric potion of a hook and loop fabric fastener, the loop fabric portion being a soft surface fabric for contacting a human body portion, and completely enclosing and containing the inner compartment to limit an amount of expansion of the inner compartment when the inner compartment is inflated; and
   fastening means being defined by a hook fabric portion of the hook and loop fabric fastener, the hook fabric portion being mounted on the outer compartment and being selectively engageable to the loop fabric portion for fastening the cuff about a human body portion.

2. The inflatable cuff of claim 1 wherein the loop fabric portion is an open weave fabric providing the soft fabric surface for contacting the human body portion.

3. The inflatable cuff of claim 1 wherein the inner compartment is comprised of a single sheet of film, folded so that a first half of the sheet overlays a second half of the sheet and the three open edges of the folded sheet are heat sealed with high energy electromagnetic waves.

4. The inflatable cuff of claim 1 wherein the hook fabric portion is secured to the loop fabric of the outer compartment by stitching.

5. The inflatable cuff of claim 1 wherein the hook fabric portion is secured to the loop fabric of the outer compartment by applying high energy electromagnetic waves to weld the hook fabric to the loop fabric.

6. The inflatable cuff of claim 1 wherein the hook fabric portion is secured to the loop fabric portion of the outer compartment by an adhesive.

7. An inflatable cuff comprising:
   an inner compartment being defined by an air-impermeable film and being closed except for an opening through which air may be caused to enter and exit the compartment;
   an outer compartment being entirely defined by a loop fabric portion of a hook and loop fabric fastener, the loop fabric portion being a soft surface fabric for contacting a human body portion, and completely enclosing and containing the inner compartment to limit an amount of expansion of the inner compartment when the inner compartment is inflated; and
   fastening means being defined by a hook fabric portion of the hook and loop fabric fastener, the hook fabric portion being mounted on the outer compartment and being selectively engageable to the loop fabric portion for fastening the cuff about a human body portion.
   wherein the inner compartment comprises a single sheet of the film and the outer compartment comprises a single sheet of the loop fabric, the film sheet being superimposed over the loop fabric sheet, the superimposed sheets being folded so that a first half of the superimposed sheets overlays a second half of the superimposed sheets with the loop fabric sheet enclosing the film sheet, and so that the three open edges of the overlaying superimposed sheets are sealed by applying high energy electromagnetic waves to fuse the overlaying superimposed sheets along the three open edges.

8. The inflatable cuff of claim 7 wherein the edges of the overlaying superimposed sheets are fused together such that the fabric sheet edges are embedded in the film sheet edges.

9. An inflatable cuff comprising:
an inner compartment being defined by an air-impermeable film and being closed except for an opening through which air may be caused to enter and exit the compartment;
an outer compartment being entirely defined by a loop fabric portion of a hook and loop fabric fastener, the loop fabric portion being a soft surface fabric for contacting a human body portion, and completely enclosing and containing the inner compartment to limit an amount of expansion of the inner compartment when the inner compartment is inflated; and
fastening means being defined by a hook fabric portion of the hook and loop fabric fastener, the hook fabric portion being mounted on the outer compartment and being selectively engageable to the loop fabric portion for fastening the cuff about a human body portion,
wherein the inner compartment comprises a single sheet of the film and the outer compartment comprises a single sheet of the loop fabric, the film sheet being superimposed over the loop fabric sheet, the film sheet and loop fabric sheet being tacked together in a plurality of spots by welding to form a composite sheet from the superimposed film sheet and loop fabric sheet, the composite sheet being folded so that a first half of the composite sheet overlays a second half of the composite sheet with the loop fabric sheet enclosing the film sheet, and so that the three open edges of the overlaying composite sheet are sealed by applying high energy electromagnetic waves to fuse the overlaying composite sheet along the three open edges.

10. The inflatable cuff of claim 9 wherein the edges of the overlaying composite sheet are fused together such that the fabric sheet edges are embedded in the film sheet edges.

11. An inflatable cuff comprising:
an inner compartment being defined by an air-impermeable film and being closed except for an opening through which air may be caused to enter and exit the compartment;
an outer compartment being entirely defined by a loop fabric portion of a hook and loop fabric fastener, the loop fabric portion being a soft surface fabric for contacting a human body portion, and completely enclosing and containing the inner compartment to limit an amount of expansion of the inner compartment when the inner compartment is inflated; and
fastening means being defined by a hook fabric portion of the hook and loop fabric fastener, the hook fabric portion being mounted on the outer compartment and being selectively engageable to the loop fabric portion for fastening the cuff about a human body portion,
wherein the inner compartment comprises two sheets of film and the outer compartment comprises two sheets of loop fabric, a first film sheet being superimposed over a first loop fabric sheet, a second film sheet being superimposed over the first film sheet, and a second loop fabric sheet being superimposed over the second film sheet such that the two loop fabric sheets encompass the two superimposed film sheets, the edges of all of the superimposed sheets being sealed together by applying high energy electromagnetic waves to fuse the superimposed sheets along the edges.

12. The inflatable cuff of claim 11 wherein the edges of the overlaying superimposed sheets are fused together such that the fabric sheet edges are embedded in the film sheet edges.

13. An inflatable comprising:
an inner compartment being defined by a single sheet of film and being closed except for an opening through which air may be caused to enter and exit the compartment;
outer compartment being entirely defined by a single sheet of loop fabric portion of a hook and loop fabric fastener, the loop fabric portion being an open weave fabric having a soft fabric surface for contacting a human body portion and completely enclosing and containing the inner compartment to limit expansion of the inner compartment when the inner compartment is inflated,
wherein the film sheet is superimposed over the loop fabric sheet, the superimposed sheets being folded so that a first half of the superimposed sheets overlays a second half of the superimposed sheets with the loop fabric sheet enclosing the film sheet, the three open edges of the overlaying superimposed sheets being sealed by fusing the overlaying superimposed sheets along the three edges to embed the fabric sheet edges in the film sheet edges; and
fastening means being defined by a hook fabric portion of the hook and loop fabric fastener, the hook fabric portion being mounted on the outer compartment and being selectively engageable to the loop fabric portion for fastening the cuff about the human body portion, the hook fabric portion being secured to the loop fabric of the outer compartment by stitching.

14. An inflatable cuff comprising:
an inner compartment being defined by a single sheet of film and being closed except for an opening through which air may be caused to enter and exit the compartment;
an outer compartment being entirely defined by a single sheet of loop fabric portion of a hook and loop fabric fastener, the loop fabric portion being an open weave soft fabric surface for contacting a human body portion, and completely enclosing and containing the inner compartment to limit expansion of the inner compartment when the inner compartment is inflated,
wherein a periphery of both the inner compartment and outer compartment are sealed together; and
fastening means being defined by a hook fabric portion of the hook and loop fabric fastener, the hook fabric portion being mounted on the outer compartment and being selectively engageable to the loop fabric portion for fastening the cuff about the human body portion.

* * * * *

UNITED STATES PATENT AND TRADEMARK OFFICE
CERTIFICATE OF CORRECTION

PATENT NO. : 5,193,549
DATED : March 16, 1993
INVENTOR(S) : MATTHEW BELLIN, SUSAN BRUNSVOLD, JOHN MOBERG It is certified that error appears in the above-identified patent and that said Letters Patent is hereby corrected as shown below:

```
     On the Title Page of the Patent, in the [56]
References Cited Section, under U.S. PATENT DOCUMENTS,
delete "3,603,304   9/1971  Werner et al.....",
insert --3,603,304  9/1971  Maier.....128/2.05--
Col. 6, line 13, after "inflatable", insert "cuff"
Col. 6, line 18, before "outer", insert --an--
```

Signed and Sealed this

Twenty-eighth Day of December, 1993

*Attest:*

BRUCE LEHMAN

*Attesting Officer*  *Commissioner of Patents and Trademarks*